United States Patent [19]

Nonn et al.

[11] Patent Number: 4,891,452

[45] Date of Patent: Jan. 2, 1990

[54] PROCESS FOR THE PREPARATION OF HYDROXYBIPHENYLS

[75] Inventors: Alain Nonn, Sainte Foy Les Lyon; Jean R. Desmurs, Communay, both of France

[73] Assignee: Rhone-Poulenc Chimie, Courbevoie, France

[21] Appl. No.: 154,194

[22] Filed: Feb. 10, 1988

[30] Foreign Application Priority Data

Feb. 12, 1987 [FR] France ................................ 87 01967

[51] Int. Cl.$^4$ ...................... C07C 39/12; C07C 37/02
[52] U.S. Cl. .................................. 568/730; 568/722; 568/744; 568/770; 568/796; 568/717
[58] Field of Search ............... 568/717, 722, 730, 744, 568/770, 796

[56] References Cited

U.S. PATENT DOCUMENTS

| | | | |
|---|---|---|---|
| 3,752,878 | 8/1973 | Kehl et al. | 423/263 |
| 4,001,340 | 1/1977 | Smith | 568/770 |
| 4,340,768 | 7/1982 | Jinbo et al. | 568/730 |
| 4,475,000 | 10/1984 | Pendery et al. | 568/730 |

FOREIGN PATENT DOCUMENTS 44-17372  7/1968  Japan .

*Primary Examiner*—Werren B. Lone
*Attorney, Agent, or Firm*—Finnegan, Henderson, Farabow, Garrett and Dunner

[57] ABSTRACT

A process for preparing hydroxybiphenyls. A bromobiphenyl is contacted with a base in aqueous liquid phase at a temperature less than or equal to 230° C. in the presence of a copper-based catalyst. The hydroxyl ion concentration of base ranges from 0.1 to about 1.6 molar equivalents per liter. At temperatures less than 215° C., a cocatalyst is preferably added.

20 Claims, No Drawings

PROCESS FOR THE PREPARATION OF HYDROXYBIPHENYLS

FIELD OF THE INVENTION

The present invention relates to a process for the manufacture of hydroxybiphenyls. More specifically, it relates to a process for the preparation of 4,4'-dihydroxybiphenyl.

BACKGROUND OF THE INVENTION 4,4'-dihydroxybiphenyl is an intermediate which is currently sought in the manufacture of synthetic materials such as polyesters, polyepoxides and polyurethanes. 4,4-dihydroxybiphenyl is also useful as an antioxidant in resins, as well as in the dyestuffs industry.

The preparation of hydroxybiphenyls by the hydrolysis of halobiphenyls using a copper catalyst, such as, for example, copper sulfate (according to U.S. Pat. No. 4,475,000) or copper oxide (according to U.S. Pat. No. 4,340,768) in an aqueous basic medium is known.

Many processes for the preparation of hydroxyaryl compounds, which are carried out in the gaseous phase, i.e., at a temperature above 300° C., in the presence of a copper-based catalyst and a rare earth phosphate-based catalyst are also known. Thus, a process for the preparation of hydroxyaryl compounds, the aryl group of which contains one or more benzene rings, starting with equivalent halogenated compounds, by hydrolysis in the presence of a catalyst based on lanthanum phosphate or cerium phosphate and copper, which are jointly precipitated in the form of an inorganic polyphosphate, is described in U.S. Pat. No. 3,752,878. This reaction is carried out as a two-phase reaction, the catalyst being in the solid form, and the halogenated compound to be hydrolyzed being in the gaseous form, because the reaction is carried out at temperatures above about 300° C. The degree of conversion of the starting compound is low and the reaction conditions are too severe for utilization on an industrial scale.

The hydrolysis of monocyclic aromatic halides at a lower temperature is shown in an abstract of Japanese Patent No. 69/17372, in which the hydrolysis is carried out at approximately 200° C., in the presence of copper derivatives having the oxidation state two, such as copper sulfate, copper dibromide and copper diacetate. The duration of the hydrolysis reaction is particularly long, and sometimes reaches 10 hours for a yield not exceeding 25%. Therefore, this method cannot be adopted on an industrial scale.

For many years, the industry has been searching for an economically viable, nonhazardous process for the preparation of hydroxybiphenyls starting with halobiphenyls.

DESCRIPTION OF THE INVENTION

The present invention has enabled this objective to be achieved. The subject of the present invention is a process, suitable for industrial application, for the preparation of a hydroxybiphenyl comprising the step of:
reacting a bromobiphenyl of the formula (I):

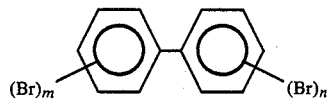

in which m and n are identical or different integers equal to 0, 1, 2 or 3 and the sum n+m of which is greater than or equal to 1 and less than or equal to 4, in an aqueous liquid phase at a temperature less than or equal to 230° C., with a base of the formula $M(OH)_p$, wherein M is a metal selected from alkali metals and alkaline-earth metals and p is an integer equal to 1 or 2 depending on the valency of the metal M, in the presence of a copper-based catalyst, and wherein the hydroxyl ion concentration in the reaction medium ranges from 0.1 to about 1.6, preferably 0.5 to 1.5, molar equivalents per liter of aqueous solution.

For example, the reaction with the dibromobiphenyl may be represented diagrammatically by the following reaction equation:

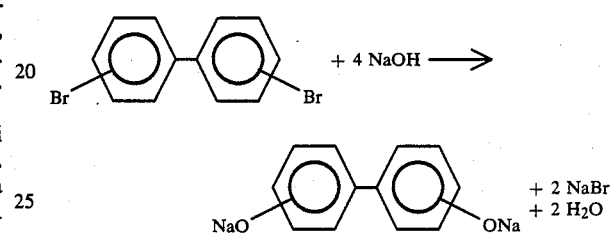

To optimize conversion of the starting material, it is necessary to have a solution containing a quantity of base capable of providing two hydroxyl radicals for each bromine atom to be hydrolyzed.

To avoid a significant decrease in reaction yield, however, the solution is not to be excessively concentrated with base. Thus, a concentration of about 1.6, preferably 1.5, molar equivalents of hydroxyl ions per liter of aqueous solution is the highest to be used. In the formula $M(OH)_p$, if p=1, such as, for example, in the case of sodium hydroxide or potassium hydroxide, the maximum molar concentration is about 1.6 moles, preferably 1.5 moles, per liter. For a base where p=2, the maximum molar concentration is about 0.8 moles, preferably 0.75 moles, per liter.

It is preferred to employ enough base so that the minimum concentration of hydroxyl ions is at least 0.1 equivalent of hydroxyl ions. This minimum concentration may be maintained by continuous or sequential addition of the base. To avoid excessive dilution of the reaction medium, if the base is to be continuously or sequentially added, concentrated base is preferably added. A preferred concentrated base is in the order of 10 N. The addition of base must keep the reaction medium within the limits defined previously.

It is also possible to introduce the bromobiphenyl continuously.

An advantage of employing relatively dilute solutions of base is found in working with a small excess of base, which avoids the use of large quantities of acid during neutralization.

The bromine starting materials may be prepared in a manner known to those skilled in the art by the action of bromine on a biphenyl at ambient temperature for a few hours. Varying the temperature, the duration, the choice of solvent and the choice of certain bromination catalysts enables one or more bromine atoms to be attached.

Among starting materials of formula (I), those in which n+m is equal to 1 or 2 are preferred. More preferred still are those in which n+m is equal to 2. Most preferred is 4,4'-dibromobiphenyl.

Among bases of formula M(OH)$_p$, the use of strong alkali metal bases, particularly sodium hydroxide or potassium hydroxide, is preferred.

As defined herein, a "copper-based" catalyst is one containing copper. The copper may be present in the elemental state or in oxidation state 1 or 2.

Representative copper-based catalysts include copper metal, copper having an oxidation state of one such as cuprous oxide, halides, acetate, cyanide, thiocyanate, trifluoromethylsulfonate and sulfide, and catalysts of copper having an oxidation state of two such as cupric oxide, halides, acetates, acetylacetonates, metaborate, isobutyrate, citrate, cyclohexylbutyrate, dimethyldithiocarbamate, hexanoate, gluconate, hydroxide, oxalate, propionate, stearate, sulfate and trifluoroacetylacetonate.

It is preferable, however, to employ copper oxides or halides having an oxidation state of one or two.

In another embodiment of the invention, it may be advantageous, particularly at reaction temperatures below 215° C., to add to the reaction medium a cocatalyst selected from
halides (particularly fluorides and bromides),
phosphates,
nitrates,
alcoholates,
inorganic or organic silicates or a source of inorganic or organic silicates,
organic sulfur-containing compounds,
carbon monoxide or a source of carbon monoxide,
alcohols (particularly methanol),
8-hydroxyquinolines,
carboxylic acids,
quaternary ammonium compounds (ammoniums),
tertiary amines (such as triethylamine and pyridines),
sulfonic acids,
cyanides,
phosphines and phosphoniums, and
palladium.

The term "source of," as used in the context of this invention encompasses those compounds which degrade in situ to form the desired cocatalyst.

Representative cocatalysts which can enable either the temperature or the duration of the reaction to be reduced, include halides, phosphates, nitrates or silicates. These compounds, when used, may be combined with protons or with cations of alkali metals, alkaline earth metals or other metals, such as copper and silver, or organic cations.

Silicates may also be prepared in situ in the reaction medium, such as by the action of a strong base on silica or on glass. Inorganic phosphates may also be prepared in situ from organic phosphates.

Representative cocatalysts which are completely organic may include alcoholates and alcohols preferably containing 1 to 12 carbon atoms, carboxylic acids containing 2 to 12 carbon atoms, sulfonic acids, for example, benzene- or pyridinesulfonic acid, tertiary amines and ammoniums, phosphines and phosphoniums, quinolines, and sulfur-containing compounds. Carbon monoxide, or a source of carbon monoxide (including organic sources, such as formates) may also be mentioned.

Examples of cocatalysts of the present invention include diphenyl sulfide, dithiophene, potassium fluoride, sodium fluoride, phosphoric acid, nitric acid, sodium methylate, methyl formate, glasses, for example Pyrex, silica, methyl orthoformate, methanol, 8-hydroxyquinoline-5-sulfonic, tetrabutylammonium bromide, triethylamine, pyridine, pyridine-sulfonic acid, benzenesulfonic acid, tetraphenylphosphonium chloride, triphenylphosphine, trisulfonated triphenylphosphine, triphenylphosphine oxide, tributylphosphine, tricyclohexylphosphine, chromium hexacarbonyl, palladium foam, and N-methylpyrrolidone.

The use of alkali metal fluorides, bromides, phosphates, nitrates, formates or silicates and of organic formates or 8-hydroxyquinolines is preferred.

With respect to reaction conditions, temperature is important from an economic standpoint. The temperature is less than or equal to 230° C. In the case where no cocatalyst is used, the temperature is preferably 215° C. to 230° C. and, preferably, concentrated base is continuously or sequentially added to the reaction medium. For temperatures less than 215° C., preferably from 180° to less than 215° C. and, more preferably, from 200° to less than 215° C., a cocatalyst is preferably used.

The pressure employed is the autogenous pressure produced by vaporizing the compounds present at the reaction temperature. Preferably, the pressure ranges from 15 to 25 bars.

The reaction time, varying with the temperature employed, preferably ranges from approximately 2 to 5 hours.

As the reaction is carried out in an aqueous medium, it is preferable to employ a mono- or polybromobiphenyl in a concentration greater than 0.15 mole per liter of water and preferably from 0.15 to 2 moles per liter of water.

The weight quantity of copper-based catalyst preferably ranges from 0.2% to 5% relative to the quantity of the bromobiphenyl introduced. The molar quantity of cocatalyst is preferably from about 0.1 to 100 times the molar quantity of catalyst. A highly excessive quantity, while not detrimental to the process of the invention, offers no additional advantage. An effective quantity can be selected by the person skilled in the art to optimize the profitability of the process.

The invention enables hydroxybiphenyls to be prepared, such as 4-hydroxybiphenyl, 2-hydroxybiphenyl, 3-hydroxybiphenyl, 4,4'-dihydroxybiphenyl, 2,2-dihydroxybiphenyl, 2,4'-dihydroxybiphenyl, 2,4,4'-trihydroxybiphenyl and tetrahydroxybiphenyls.

The following examples illustrate certain embodiments of the invention and should not be regarded as limiting the scope or spirit of the invention.

In the examples which follow, RY means the yield calculated on the material introduced into the reactor.

COMPARATIVE EXAMPLES 1 TO 4

Operating procedure

The following compounds are introduced into a 75-ml reactor made of Hastelloy C276:

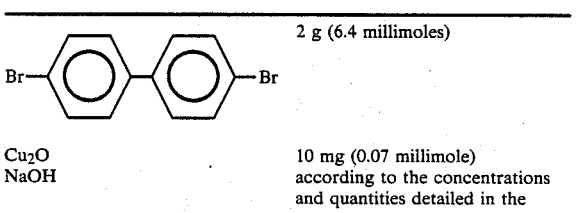

| | |
|---|---|
| | 2 g (6.4 millimoles) |
| Cu$_2$O | 10 mg (0.07 millimole) |
| NaOH | according to the concentrations and quantities detailed in the |

-continued attached table

After purging with argon and closing the autoclave, the autoclave was placed in an agitated oven and heated to the temperature shown in Table 1. After the reaction time shown in Table 1, the reactor is returned to ambient temperature. The reaction medium is diluted with 20 ml of water (reactor rinsing), acidified with 25 ml of 4N sulfuric acid and extracted with methyl isobutyl ketone (1×20 ml and 5×10 ml). The organic phase is dried over sodium sulfate. The yields are determined by high performance liquid chromatography.

TABLE 1

| Comparative Examples | NaOH concentration | T° C. | Time h | Mono OH | Di OH |
|---|---|---|---|---|---|
| Comparative 1 | 5.0 N (20 ml) | 250 | 2 | 0.3 | 39 |
| Comparative 2 | 2.5 N (20 ml) | 250 | 2 | 1.5 | 78.6 |
| Comparative 3 | 5.0 N (20 ml) | 230 | 3 | 0.05 | 15 |
| Comparative 4 | 2.5 N (20 ml) | 230 | 3 | 0.3 | 29.8 |

As can be seen, at a relatively high base concentration (5N) in Comparative Examples 1 and 3, the yield is less than 40% at 250° C. and 15% at 230° C. At even a lower base concentration (2.5N), the yield is less than 80% at 250° C. (Comparative Example 2) and only 29.8% (Comparative Example 4) at 230° C.

EXAMPLE 1 AND COMPARISON

Into the same reactor as before are introduced:

Br—⟨⟨⟩⟩—⟨⟨⟩⟩—Br    2 g (6.4 millimoles)

Cu₂O    10 mg (0.07 millimole)
1N NaOH    30 ml (30 millimoles)

Example 1 is run at 230° C. A comparison is run at 250° C. Times and yields are shown below. The results, shown below in Table 2, demonstrate that at the lower temperature within the range of the present invention, about the same yield is obtained. In view of Comparative Examples 3 and 4, shown above, Example 1 also illustrates that at a temperature of 230° C., without using a cocatalyst, a lower base concentration is needed to obtain a good yield.

TABLE 2

| Examples | T° C. | Time h | Mono OH | Di OH |
|---|---|---|---|---|
| Comparison | 250 | 2 | 5.8 | 84.5 |
| 1 | 230 | 3 | 4.1 | 82.4 |

EXAMPLES 2 AND 3 ACCORDING TO THE INVENTION

The following compounds are introduced into a reactor fitted with a Rushton central turbine stirrer (800 revolutions/min):
4,4′-dibromobiphenyl=20 g (64 millimoles)
Cu₂O=100 mg (0.7 millimole)

Concentrations of NaOH, reaction temperatures, times and yields are shown below for Examples 2 and 3 and Comparative Examples 5 and 6. The results demonstrate that at both 215° and 230°, even at a relatively low base concentration of 2.5N, without a cocatalyst, the yield is less than at a base concentration of 1.0N in accord with the invention.

TABLE 3

| Comparative Examples | NaOH concentration | T° C. | Time h | Mono OH | Di OH |
|---|---|---|---|---|---|
| Comparative 5 | 2.5 N (200 ml) | 230 | 2 | 1.5 | 70 |
| Comparative 6 | 2.5 N (200 ml) | 215 | 3 | 0 | 11.7 |
| 2 | 1.0 N (300 ml) | 230 | 2 | 5.7 | 82.4 |
| 3 | 1.0 N (300 ml) | 215 | 3 | 4.7 | 81.6 |

EXAMPLES 4 TO 7 ACCORDING TO THE INVENTION

Into the same apparatus as before are introduced:
20 g of 4,4′-dibromobiphenyl (64 millimoles)
100 mg of Cu₂O (0.7 millimole)
200 ml of 1N NaOH
Reaction temperature =215° C.

Table 4 reports Examples 4–7, wherein 10N NaOH is added sequentially. In Comparative Examples 7 and 8, no base is added sequentially. In Comparative Examples 7 and 8, a lower yield is obtained because the solution does not always contain a sufficient amount of base to provide two hydroxyl radicals for each bromine atom to be hydrolyzed. Examples 4–7 illustrate the advantage of sequentially adding concentrated base to keep the reaction medium at a hydroxyl ion concentration of about 1.5 (the concentration in Example 4 is kept at about 1.6 molar). In other words, in Examples 4–7, the hydroxyl ion content is kept near the upper limit of the process of the present invention.

TABLE 4

| Comparative Example | Reaction time before addition | Volume of 10 N NaOH added | Reaction time | Total NaOH (moles) | Total time | RY mono-OH | RY di-OH |
|---|---|---|---|---|---|---|---|
| Comparative 7 | — | — | — | 0.2 | 3 h | 0.1 | 53.1 |
| Comparative 8 | — | — | — | 0.2 | 2 h | 0.3 | 47.8 |
| 4 | 1 h | 30 ml | 1 h | 0.5 | 2 h | 0.6 | 56.1 |
| 5 | 0.75 h | 5 ml | 0.25 h | — | — | — | — |
|  | — | 5 ml | 0.75 h | 0.3 | 2 h | 0.7 | 57.9 |
| 6 | 0.75 h | 5 ml | 0.50 h | — | — | — | — |
|  | — | 5 ml | 0.25 h | — | — | — | — |
|  | — | 5 ml | 0.50 h | 0.35 | 2 h | 0.8 | 61.2 |
| 7 | 1 h | 5 ml | 0.70 h | — | — | — | — |
|  | — | 5 ml | 0.70 h | — | — | — | — |
|  | — | 5 ml | 0.70 h | 0.35 | 3 h | 1.6 | 81.8 |

EXAMPLE 8

TABLE 5

| Charge: | 20 g of 4,4'-dibromobiphenyl (0.064 mole) |  |  |
|---|---|---|---|
|  | 300 ml of 1 N NaOH (0.300 mole) |  |  |
|  | 100 mg of $Cu_2O$ |  |  |
| Conditions: | 200° C. 3 h |  |  |
|  | stirring 800 revolutions/min. |  |  |
| Additive* | RY (%) 4-OH | RY (%) 4,4'-diOH | TT diBr |
| Without | 0.9 | 35.0 | 44.6 |
| 8-Hydroxy quinoline | — | 57.7 | — |

*2 moles/mole of catalyst

Example 8 demonstrates that at a temperature of 200° C., even at a low base concentration of 1N, the yield is significantly improved by the presence of cocatalyst.

We claim:

1. A process for the preparation of a hydroxybiphenyl comprising the step of:
reacting a bromobiphenyl of the formula (I):

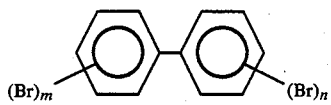

in which m and n are identical or different integers equal to 0, 1, 2 to 3 and the sum n+m of which is greater than or equal to 1 and less than or equal to 4, in an aqueous liquid phase at a temperature less than or equal to 230° C., with a base of the formula $M(OH)_p$, wherein M is a metal selected from the alkali metals and alkaline-earth metals and p is an integer equal to 1 or 2 depending on the valency of the metal M, in the presence of a copper-based catalyst, and wherein the hydroxyl ion concentration in the reaction medium ranges from 0.1 to about 1.6 molar equivalents per liter of aqueous solution and further wherein the hydroxyl ion concentration, relative to the bromobiphenyl concentration, is sufficient to provide at least two hydroxyl radicals for each bromine atom of said bromobiphenyl.

2. The process of claim 1, wherein said hydroxyl ion concentration ranges from 0.5 to 1.5 molar equivalents per liter.

3. The process of claim 1, wherein said temperature ranges from 215° C. to 230° C.

4. The process of claim 1, wherein in the formula (I), n+m is equal to 1 or 2.

5. The process of claim 1, wherein the compound of formula (I) is 4,4'-dibromobiphenyl.

6. The process of claim 1, wherein the copper-based catalyst is selected from oxides or halides of copper in the oxidation state of one or two.

7. The process of claim 1, wherein the concentration of hydroxyl ions in the reaction medium is maintained within the 0.1 to about 1.6 range by continuous or sequential addition of base to the reaction medium.

8. The process of claim 7, wherein concentrated base is added sequentially to the reaction medium.

9. The process of claim 8, wherein said base is approximately 10N.

10. The process of claim 7, wherein approximately 10N base is added continuously.

11. The process of claim 1, wherein the bromobiphenyl and the base are introduced into the reaction medium continuously.

12. A process for the preparation of a hydroxybiphenyl, comprising the step of reacting a bromobiphenyl of the formula (I):

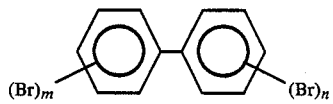

in which m and n are identical or different integers equal to 0, 1, 2 or 3, and the sum n+m of which is greater than or equal to 1 and less than or equal to 4, in an aqueous liquid phase at a temperature less than 215° C., with a base of the formula $M(OH)_p$, wherein M is a metal selected from the alkali metals and alkaline earth metals and p is an integer equal to 1 or 2 depending on the valency of M, in the presence of a copper-based catalyst and a rocatalyst selected from halides, phosphates, nitrates, alcoholates, inorganic or organic silicates or sources of inorganic or organic silicates, alcohols, carboxylic acids, sulfonic acids, organic sulfur-containing compounds, carbon monoxide or a source of carbon monoxide, 8-hydroxyquinolines, ammoniums, tertiary amines, phosphines, phosphoniums, cyanides and palladium, and wherein the hydroxyl ion concentration in the reaction medium ranges from 0.1 to about 1.6 molar equivalents per liter of aqueous solution and further wherein the hydroxyl ion concentration, relative to the bromobiphenyl concentration, is sufficient to provide at least two hydroxyl radicals for each bromine atom of said bromobiphenyl.

13. The process of claim 12, wherein the hydroxyl ion concentration ranges from 0.5 to 1.5 molar equivalents per liter.

14. The process of claim 12, wherein said temperature ranges from 180° C. to less than 215° C.

15. The process of claim 12, wherein said temperature ranges from 200° C. to less than 215° C.

16. The process of claim 12, wherein the cocatalyst is added in a molar ratio ranging from 0.1 to 100 calculated relative to the catalyst.

17. The process of claim 12, wherein the temperature is 200° C.

18. The process of claim 17, wherein said hydroxyl concentration is about 1 molar equivalent per liter of aqueous solution.

19. The process of claim 12, wherein in the formula (I), n+m is equal to 1 or 2.

20. The process of claim 12, wherein the compound of formula (I) is 4,4'-dibromobiphenyl.

* * * * *

UNITED STATES PATENT AND TRADEMARK OFFICE
CERTIFICATE OF CORRECTION

PATENT NO. : 4,891,452

DATED : January 2, 1990

INVENTOR(S) : Alain Nonn et al

It is certified that error appears in the above-identified patent and that said Letters Patent is hereby corrected as shown below:

Claim 12, col. 8, line 27, "rocatalyst" should be --cocatalyst--.

Signed and Sealed this

Twenty-fifth Day of August, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,891,452

DATED : January 02, 1990

INVENTOR(S) : Alain Nonn et al

It is certified that error appears in the above-identified patent and that said Letters Patent is hereby corrected as shown below:

Claim 12, Col. 8, Line 27, "rocatalyst" should be --cocatalyst--.

Claim 12, Col. 8, Lines 27-34, "halides, phosphates,... and palladium" should be --diphenyl sulfide, dithiophene, potassium fluoride, sodium fluoride, phosphoric acid, nitric acid, sodium methylate, methyl formate, silica, methyl orthoformate, methanol, 8-hydroxyquinoline-5-sulfonic, tetrabutylammonium bromide, triethylamine, pyridine, pyridine-sulfonic acid, benzene-sulfonic acid, tetraphenylphosphonium chloride, triphenylphosphine, trisulfonated triphenylphosphine, triphenylphosphine oxide,

UNITED STATES PATENT AND TRADEMARK OFFICE
CERTIFICATE OF CORRECTION

PATENT NO. : 4,891,452

DATED : January 02, 1990

INVENTOR(S) : Alain Nonn, et al

It is certified that error appears in the above-identified patent and that said Letters Patent is hereby corrected as shown below:

tributylphosphine, tricyclohexylphosphine, chromium hexacarbonyl, palladium foam and N-methylpyrrolidone--.

This certificate supersedes Certificate of Correction issued August 25, 1992.

Signed and Sealed this

Twenty-second Day of December, 1992

*Attest:*

DOUGLAS B. COMER

*Attesting Officer*     Acting Commissioner of Patents and Trademarks